(12) United States Patent
Lu et al.

(10) Patent No.: US 9,809,476 B2
(45) Date of Patent: Nov. 7, 2017

(54) BIOLOGICAL COMPOSITE MATERIAL LOADED WITH MAGNETIC NANOPARTICLES WITH CORE-SHELL STRUCTURE, THE PREPARATION THEREFORE AND THE APPLICATION

(71) Applicant: Soochow University, Suzhou, Jiangsu (CN)

(72) Inventors: Jianmei Lu, Jiangsu (CN); Dongyun Chen, Jiangsu (CN)

(73) Assignee: Soochow University, Suzhou (CN)

( * ) Notice: Subject to any disclaimer, the term of this patent is extended or adjusted under 35 U.S.C. 154(b) by 0 days.

(21) Appl. No.: 15/382,629

(22) Filed: Dec. 17, 2016

(65) Prior Publication Data

US 2017/0174542 A1 Jun. 22, 2017

(30) Foreign Application Priority Data

Dec. 17, 2015 (CN) .......................... 2015 1 0957405

(51) Int. Cl.

| | |
|---|---|
| *C02F 3/10* | (2006.01) |
| *C02F 3/34* | (2006.01) |
| *B01J 13/04* | (2006.01) |
| *C01G 49/08* | (2006.01) |
| *C02F 1/48* | (2006.01) |
| *C12N 1/20* | (2006.01) |
| *C02F 101/22* | (2006.01) |

(52) U.S. Cl.
CPC ................. *C02F 3/34* (2013.01); *B01J 13/04* (2013.01); *C01G 49/08* (2013.01); *C02F 1/48* (2013.01); *C12N 1/20* (2013.01); *C01P 2004/04* (2013.01); *C01P 2004/64* (2013.01); *C01P 2004/84* (2013.01); *C01P 2006/42* (2013.01); *C02F 2101/22* (2013.01); *C02F 2305/08* (2013.01)

(58) Field of Classification Search
CPC ....... C10G 1/047; C10G 33/04; B01F 5/0463; B01F 5/0466; B82Y 30/00; B01J 20/0229; B01J 20/28009; C01G 49/06; C02F 1/281; Y10S 977/838; Y10S 977/773
USPC .................................. 210/732; 977/773, 838
See application file for complete search history.

(56) References Cited

U.S. PATENT DOCUMENTS 3,141,738 A * 7/1964 Kagitani ................ C01G 49/08
423/632

OTHER PUBLICATIONS

Ali et al, Synthesis, characterization, applications, and challenges of iron oxide nanoparticles Aug. 19, 2016, Dovepress, vol. 2016:9, p. 52.*

Carmago et al, In vitro reduction of hexavalent chromium by a cell-free extract of *Bacillus* sp. ES 29 stimulated by Cu2+ Apr. 3, 2003, Springer-Verlag, vol. 62, p. 569.*

(Continued)

*Primary Examiner* — Claire A Norris
(74) *Attorney, Agent, or Firm* — SZDC Law P.C.

(57) ABSTRACT

A preparation method of *Bacillus subtilis* biological composite material loaded with $Fe_3O_4$ magnetic nanoparticles with core-shell structure includes the following steps: 1) preparation of $Fe_3O_4$ nanoparticles, 2) preparation of $Fe_3O_4@mSiO_2$ nanoparticles, 3) preparation of $Fe_3O_4@mSiO_2@MANHE$ nanoparticles; and 4) preparation of *Bacillus subtilis*$@Fe_3O_4@mSiO_2@MANHE$ composite.

10 Claims, 4 Drawing Sheets

(56) References Cited

OTHER PUBLICATIONS

Dongyun Chen et al, Modification of magnetic silica/iron oxide nnocomposites with fluorescent polymethacrylic acid for cancer targeting and drug delivery Jun. 23, 2010, The Royal Society of Chemistry, vol. 20, p. 6422-6424.*

Ling Chen et al, Azo-functionalized Fe3O4 nanoparticles: a near-infrared light triggered drug delivery system for combined therapy of cancer with low toxicity Apr. 20, 2016, The Royal Society of Chemistry, vol. 4, p. 3660-3662.*

Khoee et al, A new procedue for precipitation of polyethylene glycol-grafted magnetic iron oxide nanoparticles Jun. 11, 2014, Springer-Verlag, vol. 4, p. 111 1-2.*

Khosroshahi et al, Amino surface modification of Fe3O4/SiO2 nanoparticles for bioengineering applications Nov. 12, 2013, Taylor & Francis Online, vol. 27, p. 573-575.*

Patsula et al, Superparamagnetic Fe3O4 nanoparticles: Synthesis by thermal decomposition of iron(III) glucuronate and application in magnetic resonance imaging Feb. 29, 2016, American Chemical Society, vol. 8, p. 7238-7240.*

Wang et al, Bacterial reduction of hexavalent chromium 1995, Springer-Verlag, vol. 14, p. 160-161.*

Xu et al, Use of iron oxide nanomaterials in wastewater treatment: A review Mar. 4, 2012, Elsevier, vol. 424, p. 4-5.*

Yan et al, Bio-template route for the facile fabrication of TiO2@Bacillus subtilis composite particles and their application for the degradation of rhodamine B Mar. 18, 2015, Springer-Verlag, vol. 145, p. 1302.*

\* cited by examiner

BIOLOGICAL COMPOSITE MATERIAL LOADED WITH MAGNETIC NANOPARTICLES WITH CORE-SHELL STRUCTURE, THE PREPARATION THEREFORE AND THE APPLICATION

This application claims priority to Chinese Patent Application No.: 201510957405.9, filed on Dec. 17, 2015, which is incorporated by reference for all purposes as if fully set forth herein.

TECHNICAL FIELD

The present invention belongs to the technical field functional materials, the specific involves a load of magnetic nanoparticles with core-shell structure biological composite material, the preparation method of the composite material, and the use of the composite material to deal with the use of wastewater containing hexavalent chromium.

BACKGROUND TECHNOLOGY

Hexavalent chromium (abbreviated to Cr (VI)) as the swallowed poison/aspiration is extremely toxic, sensitization, birth defects, cancer and other serious consequences, and a lasting dangers to the environment. Unfortunately, chromium is widely used in numerous industrial processes, including leather tanning, pigment production, electroplating and ore refining. Because of extremely toxic and high solubility, hexavalent chromium goes into the living cells easily and produces reactive oxygen species (ROS), resulting in serious oxidative injuries to cell constituents. The main effects of hexavalent chromium for humans are dermatitis and aggressive reaction in lungs and nasal septum. So for treatment of wastewater containing hexavalent chromium needs to be received extensive attention of the society from all walks of life.

Due to have a combination of magnetic particles and the double advantage of nanoparticles, $Fe_3O_4$ magnetic nanoparticles have been widely applied in targeting drug carrier, cell separation, magnetic resonance, immunoassay, nucleic acid hybridization and biomedical fields. At the same time, the super paramagnetic material in the field of environmental protection monitoring also has the very good application prospect, can be used as adsorption material to deal with industrial waste water of heavy metal. However, magnetic $Fe_3O_4$ nanoparticles is difficult to be applied due to its easy oxidation, strong tendency of gathering, difficult to direct application.

In recent years, with clean and no secondary pollution and low cost advantage, such as biological method has gained extensive attention, but microbial processing pollutants also has its own disadvantages, processing cycle is long, the bacteria difficult separation from water and other factors restricted the practical application.

SUMMARY OF THE INVENTION

In view of the above, the invention combines the advantages of the adsorption method and the biodegradation method, and combines the two by modifying the $Fe_3O_4$ magnetic nanoparticles to the surface of *Bacillus subtilis* through the polymer shell covering the magnetic nanoparticle core, Cr(VI) can be rapidly enriched by the magnetic nanoparticles, and Cr (VI) can be rapidly degraded by microorganisms which are supported on the surface. The magnetic properties of the nanoparticles themselves can be separated rapidly from the water, which can overcome the bottleneck of its application and make it widely used in the treatment of heavy metal pollution.

First, the present invention provides a method for preparing a *Bacillus subtilis* biocomposite loaded with $Fe_3O_4$ magnetic nanoparticles having a core-shell structure, comprising the following steps:

(1) Preparation of $Fe_3O_4$ Nanoparticles

In this experiment, all the chemical agents were of analytical grade and were used without further purification. The spherical magnetic particles were prepared according to the literature with some modification. As usually, 2.02 g of $Fe(NO_3)_3 \cdot 9H_2O$ and 4.1 g of sodium acetate were dissolved in 50 mL of ethylene glycol (EG) with stirring for 30 min. The obtained solution was transferred to a Teflon-lined stainless-steel autoclave and heated at 180° C. for 6 h. Then the autoclave was naturally cooled to room temperature. The gained black magnetite particles were washed with ethanol for several times, and dried in vacuum at 60° C. for 5 h.

(2) Synthesis of $Fe_3O_4@mSiO_2$

The core-shell structured $Fe_3O_4@mSiO_2$ microspheres were prepared through a modified Stöber method. In a typical process, 0.10 g of obtained $Fe_3O_4$ particles were treated using 0.1 M HCl solution by ultrasonication for 20 min. Whereafter, the treated $Fe_3O_4$ particles were separated via centrifugation, washed with deionized water. At the same time, The $Fe_3O_4$ was dispersed in the mixture solution of 80 mL of ethanol, 20 mL of deionized water, and 1.0 mL of concentrated ammonia aqueous solution (28 wt. %). Afterward, 0.3 g of cetyltrimethylammonium bromide (CTAB) was added dropwise to the solution. After this, 0.25 mL TEOS was added dropwise into the solution under vigorous stirring for 6 h. After reaction for 6 h, the product was collected by magnetic separation and tautologically washed with ethanol and deionized water. The above coating process was redone twice. The structure-directing agent (CTAB) was removed with ethanol and deionized water for three times. The obtained precipitate was separated and washed with deionized water. Subsequently, the product was dried in vacuum at 60° C. for 24 h. The manufactured microspheres what was called $Fe_3O_4@mSiO_2$.

(3) Synthesis of $Fe_3O_4@mSiO_2@MANHE$ 200 mg ($Fe_3O_4@mSiO_2$) of the nanoparticles obtained for 250 ml flask, the flask to add 150 ml acetonitrile, ultrasound 30 min, then add 3 ml KH550, mechanical agitation for the night.

The acid chloride derivative of ABCPA (Cl-ABCPA) was prepared by a reaction of ABCPA and $PCl_5$. ABCPA (3.0 g) was dissolved in dichloromethane (25 mL) and cooled to 0° C. $PCl_5$ (24 g) in 25 mL of $CH_2Cl_2$ was added into the above solution and stirred overnight. After the reaction, the excess $PCl_5$ was removed by filtration. The clear solution was added into 5-fold of hexane at 0° C., and 4,4-azo-bis(4-cyanopentanoicchloride) was obtained after filtration. $Fe_3O_4mSiO_2$—$NH_2$ nanoparticles (0.600 g) were added to 80 mL of dry dimethylformamide. After 0.5 h of ultrasonication, $Fe_3O_4@mSiO_2$—$NH_2$ (0.60 g) was dispersed in a mixture of 80 mL of $CH_2Cl_2$ and 2 mL of triethylamine, and Cl-ABCPA (2.5 g) in 25 mL of dry $CH_2Cl_2$ was added to the dispersion. After stirring at 0° C. for 2 h, the dispersion was stirred at room temperature overnight. $Fe_3O_4@mSiO_2$-AB- CPA was obtained after filtration and washing with methanol and dichloromethane. Polymer on $Fe_3O_4$@$mSiO_2$-ABCPA sheets were prepared by free-radical polymerization. In a Schlenk flask, $Fe_3O_4$@$mSiO_2$-ABCPA (0.05 g), 4-vinylpyridine (4 mL) and N-Acryloxysuccinimide (0.7 g) monomer were dissolved in 9 mL of Cyclohexanone. After 0.5 h min sonication, the dispersion was stirred at 75° C. for 5 h. The resulting product was dissolved in acetone and centrifuged to remove the free polymer chains which were not anchored to the nanoparticles. The final product (FSM) was dried in vacuum at 50° C.

(4) Synthesis of Bacterial@$Fe_3O_4$@$mSiO_2$@MANHE

After strain B. subtilis ATCC-6633 was cultured for 48 h in 100 mL LB medium with shaking (120 rpm), the B. subtilis ATCC-6633 were harvested by centrifugation (5 min, 5500 g) and washed twice with PBS (sterile phosphate buffer solution). Then, the cell pellets were resuspended in PBS. Subsequently, 30 mg FSM was added into above system. Planktonic cells were cultivated at 30° C. with shaking (120 rpm) for 5 h. After that, BFSM were obtained by magnetic separation.

Preferably, in the above production process, the molar ratio between the ferrous sulfate heptahydrate and anhydrous sodium acetate in step (1) is 1:7.

Preferably, in the above-mentioned production method, the volume ratio of ethanol to water in the mixed solution of ethanol and water in step (2) is 4:1.

Preferably, in the above production method, the water used in the mixture of ethanol and water in step (2) is deionized water.

Preferably, in the above production method, the mass ratio between $Fe_3O_4$ nanoparticles, cetyltrimethylammonium bromide, and tetraethoxysilane in step (2) is 1:3:2.3.

Preferably, in the above preparation method, the ratio between the $Fe_3O_4$@$mSiO_2$ nanoparticles and the aminopropyltriethoxysilane in the step (3) is 200 mg:3 mL.

Preferably, in the above preparation method, the mass ratio between the amino-modified $Fe_3O_4$@$mSiO_2$ nanoparticles and 4,4'-azobis (4-cyanovaleryl chloride) in the step (3) is 1:20.

Preferably, in the above-mentioned production method, the mass ratio of the ABCPA-modified $Fe_3O_4$@$mSiO_2$ nanoparticles to the N-acryloyloxysuccinimide in step (3) is 1:20.

Preferably, in the above-mentioned production method, the ratio between the N-acryloyloxysuccinimide and the 4-vinylpyridine in step (3) is 1 g:10 mL.

Preferably, in the above production method, the inert gas in the step (3) is selected from any one of nitrogen, helium, and argon, preferably nitrogen.

Preferably, in the above preparation method, the mass ratio between the Bacillus subtilis (wet weight) and $Fe_3O_4$@$mSiO_2$@MANHE nanoparticles in step (4) is 100:1.

Preferably, in the above-mentioned production method, the PBS solution in step (4) has a pH of 7.

Secondly, the present invention provides a Bacillus subtilis biological composite material loaded with $Fe_3O_4$ magnetic nanoparticles having a core-shell structure prepared by the above-mentioned preparation method.

Finally, the present invention provides the use of a Bacillus subtilis biocomposite loaded with $Fe_3O_4$ magnetic nanoparticles having a core-shell structure as described above in the treatment of wastewater containing hexavalent chromium.

Compared with the prior art, the invention adopting the technical proposal has the following advantages:

(1) the raw materials used in the preparation process are inexpensive and easy to obtain;

(2) the operation is simple and convenient, the whole process does not use expensive equipment;

(3) The composite material of the invention has good adsorption degradation effect on Cr (VI) in water, and can be separated from water body quickly without causing secondary pollution and has wide application prospect.

APPENDED DRAWINGS

DETAILED DESCRIPTION

The following will be combined with the appended drawings and the implementation of the specific case to make further explanation of the invention. Unless specifically noted that agents used in the following example, experimental material and equipment, etc. Can be obtained through commercial means.

Example 1: Preparation of $Fe_3O_4$ Nanoparticles

In this experiment, all the chemical agents were of analytical grade and were used without further purification. The spherical magnetic particles were prepared according to the literature with some modification.[40] As usually, 2.02 g of $Fe(NO_3)_3 \cdot 9H_2O$ and 4.1 g of sodium acetate were dissolved in 50 mL of ethylene glycol (EG) with stirring for 30 min. The obtained solution was transferred to a Teflon-lined stainless-steel autoclave and heated at 180° C. for 6 h. Then the autoclave was naturally cooled to room temperature. The gained black magnetite particles were washed with ethanol for several times, and dried in vacuum at 60° C. for 5 h.

Figure 1:
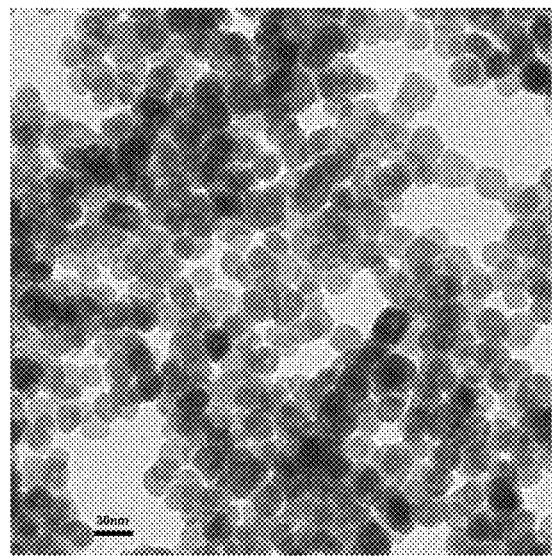
FIG. 1 shows the transmission electron microscopy (TEM) of $Fe_3O_4$ nanoparticles.

FIG. 1 shows the TEM of $Fe_3O_4$ nanoparticles. It can be seen, $Fe_3O_4$ nanoparticles dispersed and diameter of about 30 nm.

Example 2: Preparation of $Fe_3O_4$@$mSiO_2$ Nanoparticles

The core-shell structured $Fe_3O_4$@$mSiO_2$ microspheres were prepared through a modified Stöber method. In a typical process, 0.10 g of obtained $Fe_3O_4$ particles were treated using 0.1 M HCl solution by ultrasonication for 20 min. Whereafter, the treated $Fe_3O_4$ particles were separated via centrifugation, washed with deionized water. At the same time, The $Fe_3O_4$ was dispersed in the mixture solution of 80 mL of ethanol, 20 mL of deionized water, and 1.0 mL of concentrated ammonia aqueous solution (28 wt. %). Afterward, 0.3 g of cetyltrimethylammonium bromide (CTAB) was added dropwise to the solution. After this, 0.25 mL TEOS was added dropwise into the solution under vigorous stirring for 6 h. After reaction for 6 h, the product was collected by magnetic separation and tautologically washed with ethanol and deionized water. The above coating process was redone twice. The structure-directing agent (CTAB) was removed with ethanol and deionized water for three times. The obtained precipitate was separated and washed with deionized water. Subsequently, the product was dried in vacuum at 60° C. for 24 h. The manufactured microspheres what was called $Fe_3O_4@mSiO_2$.

Figure 2:
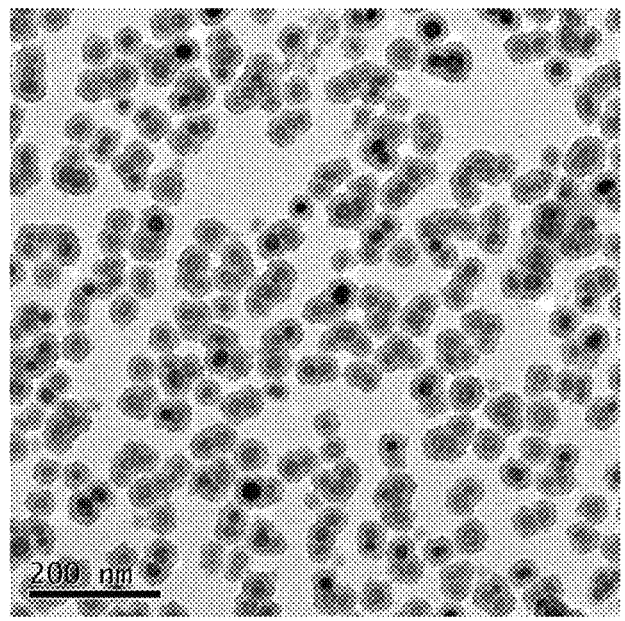
FIG. 2 shows the transmission electron microscopy (TEM) of $Fe_3O_4$@$mSiO_2$ nanoparticles.

FIG. 2 shows the TEM of $Fe_3O_4@mSiO_2$ nanoparticles. It can be seen that $Fe_3O_4$ surface coated with mesoporous silica (mesoporous silicon dioxide, abbreviated as $mSiO_2$), and has good dispersion, the diameter of nanoparticles increased to 50 nm.

Example 3: Preparation of $Fe_3O_4@mSiO_2@MANHE$ Nanoparticles 200 mg ($Fe_3O_4@mSiO_2$) of the nanoparticles obtained for 250 ml flask, the flask to add 150 ml acetonitrile, ultrasound 30 min, then add 3 ml KH550, mechanical agitation for the night.

The acid chloride derivative of ABCPA (Cl-ABCPA) was prepared by a reaction of ABCPA and $PCl_5$. ABCPA (3.0 g) was dissolved in dichloromethane (25 mL) and cooled to 0° C. $PCl_5$ (24 g) in 25 mL of $CH_2Cl_2$ was added into the above solution and stirred overnight. After the reaction, the excess $PCl_5$ was removed by filtration. The clear solution was added into 5-fold of hexane at 0° C., and 4,4-azo-bis(4-cyanopentanoicchloride) was obtained after filtration. $Fe_3O_4mSiO_2$—$NH_2$ nanoparticles (0.600 g) were added to 80 mL of dry dimethylformamide. After 0.5 h of ultrasonication, $Fe_3O_4@mSiO_2$—$NH_2$ (0.60 g) was dispersed in a mixture of 80 mL of $CH_2Cl_2$ and 2 mL of triethylamine, and Cl-ABCPA (2.5 g) in 25 mL of dry $CH_2Cl_2$ was added to the dispersion. After stirring at 0° C. for 2 h, the dispersion was stirred at room temperature overnight. $Fe_3O_4@mSiO_2$-ABCPA was obtained after filtration and washing with methanol and dichloromethane. Polymer on $Fe_3O_4@mSiO_2$-ABCPA sheets were prepared by free-radical polymerization. In a Schlenk flask, $Fe_3O_4@mSiO_2$-ABCPA (0.05 g), 4-vinylpyridine (4 mL) and N-Acryloxysuccinimide (0.7 g) monomer were dissolved in 9 mL of Cyclohexanone. After 0.5 h min sonication, the dispersion was stirred at 75° C. for 5 h. The resulting product was dissolved in acetone and centrifuged to remove the free polymer chains which were not anchored to the nanoparticles. The final product (FSM) was dried in vacuum at 50° C.

Figure 3:
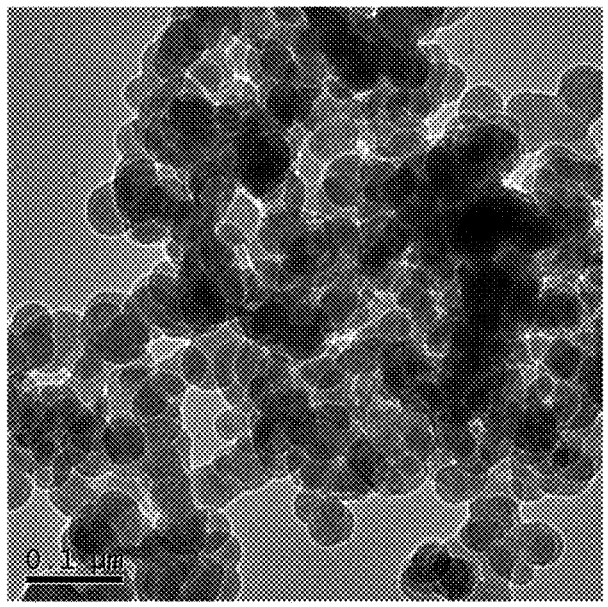
FIG. 3 shows the transmission electron microscopy (TEM) of $Fe_3O_4$@$mSiO_2$@MANHE nanoparticles.

FIG. 3 shows the TEM of $Fe_3O_4@mSiO_2@MANHE$ nanoparticles. As can be seen from the figure, $Fe_3O_4@mSiO_2$ nanoparticles coated with a layer of polymer (MANHE), dispersion decreased, the diameter of nanoparticles to further increase to 100 nm.

Example 4: Culture of *Bacillus subtilis* and Degradation of Cr (VI)

*B. subtilis* ATCC-6633 was obtained from Fujian Institute of Microbiology, China. Previous study suggested that the maximum hexavalent chromium resistance of *B. subtilis* ATCC-6633 is 40 mg/L. Planktonic cells were grown at 30° C. with shaking (120 rpm) for 48 h in modified LuriaeBertani (LB) liquid medium (pH=7) supplemented with 5 g/L NaCl, 10 g/L tryptone, 5 g/L yeast extract and 5 g/L glucose.

Figure 4:
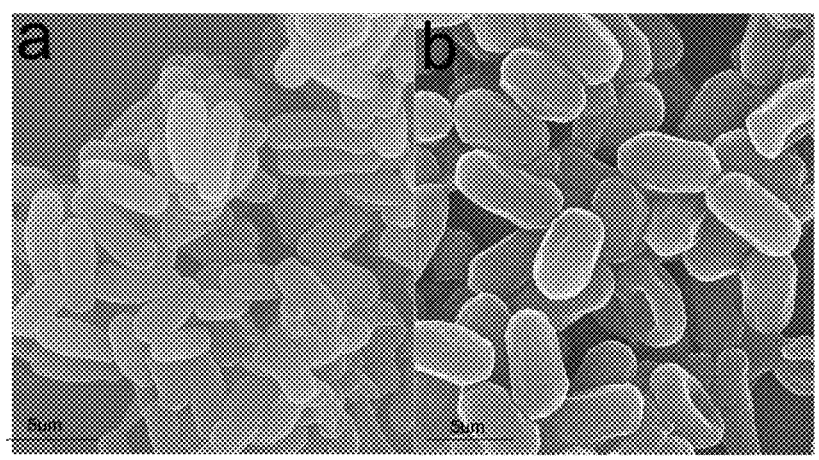
FIG. 4 is a scanning electron microscopy (SEM) image of Bacillus subtilis before and after treatment of Cr (VI).

FIG. 4a shows the SEM of *Bacillus subtilis* Cr (VI), FIG. 4b shows the SEM of *Bacillus subtilis* after Cr (VI) degradation. From the figure, it can be seen that the surface of the cell before Cr (VI) was smooth and the surface of the cell after Cr (VI) was irregular.

Example 5: Preparation of *Bacillus subtilis*@$Fe_3O_4@mSiO_2@MANHE$ Composite

After strain *B. subtilis* ATCC-6633 was cultured for 48 h in 100 mL LB medium with shaking (120 rpm), the *B. subtilis* ATCC-6633 were harvested by centrifugation (5 min, 5500 g) and washed twice with PBS (sterile phosphate buffer solution). Then, the cell pellets were resuspended in PBS. Subsequently, 30 mg FSM was added into above system. Planktonic cells were cultivated at 30° C. with shaking (120 rpm) for 5 h. After that, BFSM were obtained by magnetic separation.

Figure 5:
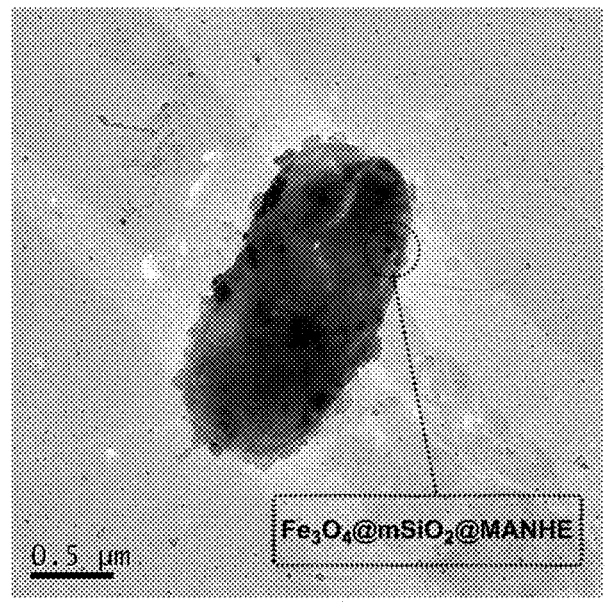
FIG. 5 shows the transmission electron microscopy (TEM) of the B. subtilis@$Fe_3O_4$@$mSiO_2$@MANHE composite.

FIG. 5 shows the TEM of a *B. subtilis*@$Fe_3O_4@mSiO_2@MANHE$ composite. It is clear from the figure that $Fe_3O_4@mSiO_2@MANHE$ nanoparticles are modified to the surface of the cell.

Example 6: Degradation of Cr (VI) (Concentration 40 ppm) by *Bacillus subtilis* and Test Results The bacterial cells were collected by centrifugation and re-dispersed in waste water (100 mL) containing 40 ppm Cr (VI) and sampled at different times. The concentration of the solution at each time was measured by colorimetry and the UV-Spectrum.

Figure 6:
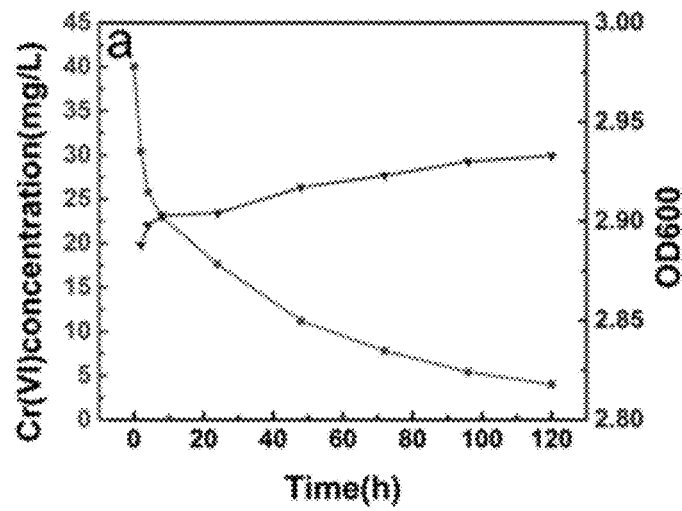
FIG. 6 is the degradation curve of Cr (VI) and the OD600 curve of B. subtilis.
Figure 7:
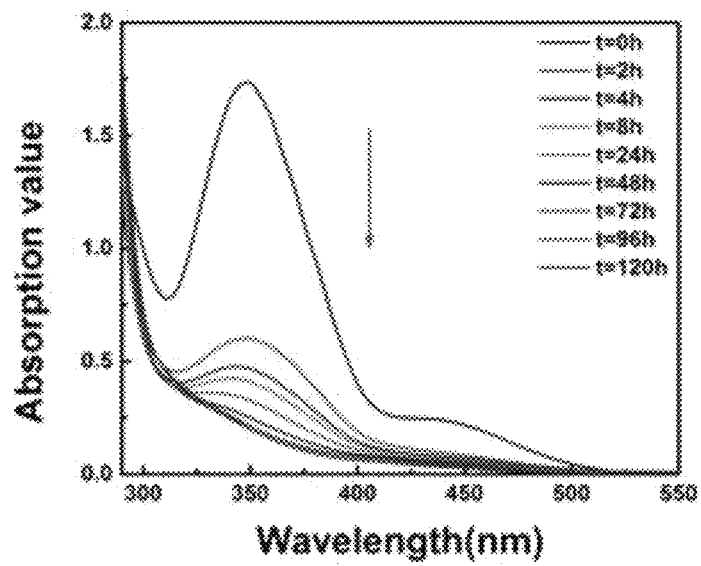
FIG. 7 shows the UV-Vis absorption spectra of Cr (VI) treated with B. subtilis at different times.

FIG. 6 shows the degradation curve and OD600 curve of Cr (VI) treated by *Bacillus subtilis*. It can be seen that the concentration of Cr (VI) decreased and the OD600 of bacteria increased on the original basis, which indicated that *Bacillus subtilis* could tolerate Cr (VI) VI) can effectively survive in Cr (VI)-containing water. FIG. 7 shows the UV-Vis absorption spectra of Cr (VI) treated with *Bacillus subtilis* at different times. It can be seen that at 364 nm, the maximum absorption wavelength decreases with time, which indicates that the concentration of Cr (VI), And no absorption peak after 120 h. At 364 nm, the concentration of Cr (VI) in the surface solution has almost reached zero.

Example 7: Effect Comparison of Treatment of Cr (VI) (Concentration 40 ppm) with *Bacillus subtilis*, $Fe_3O_4@mSiO_2@MANHE$ Nanoparticles, *Bacillus subtilis*@$Fe_3O_4@mSiO_2@MANHE$ Composite $Fe_3O_4@mSiO_2@MANHE$ nanoparticles and *Bacillus subtilis*@$Fe_3O_4@mSiO_2@MANHE$ composites were weighed and dispersed in 40 ppm Cr (VI) solution. Samples were taken at different times and samples were taken and the corresponding UV-Vis absorption spectra were plotted.

Figure 8:
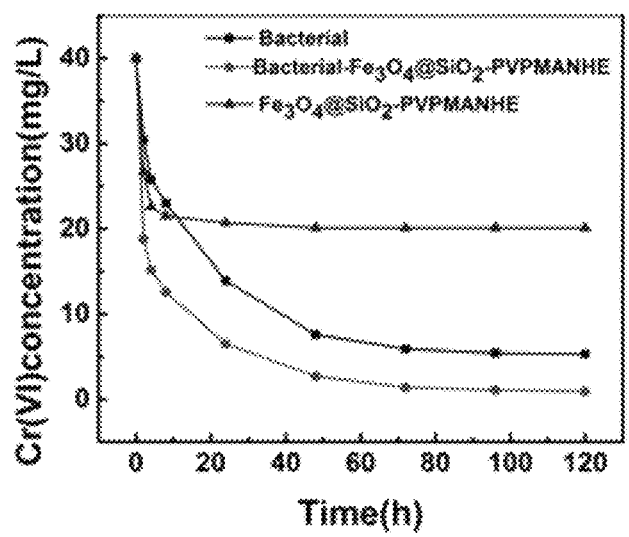
FIG. 8 shows the degradation of Cr (VI) by Bacillus subtilis, $Fe_3O_4$@$mSiO_2$@MANHE nanoparticles and Bacillus subtilis @$Fe_3O_4$@$mSiO_2$@MANHE composite.

FIG. 8 shows the degradation of Cr (VI) by *Bacillus subtilis*, $Fe_3O_4@mSiO_2@MANHE$ nanoparticles and *Bacillus subtilis*@$Fe_3O_4@mSiO_2@MANHE$ composite. It is clear from the comparison that *Bacillus subtilis*@$Fe_3O_4@mSiO_2@MANHE$ composite has the highest removal rate of hexavalent chromium and the best effect.

In summary, the present invention realizes the degradation of Cr (VI) by adsorption on the side of $Fe_3O_4@mSiO_2@MANHE$ nanoparticle to *Bacillus subtilis*, and has high degradation speed and high removal efficiency. More importantly, to achieve the magnetic separation of bacteria to solve the obstruction of microbial treatment of heavy metal pollution application problems. In addition, the production method disclosed in the present invention is easy to handle and the raw materials used are inexpensively available. Therefore, the magnetic nanometer biological composite material of the invention will have good application prospect in the future sewage treatment.

The invention claimed is:

1. A preparation method of a *Bacillus subtilis* biological composite material loaded with $Fe_3O_4$ magnetic nanoparticles with core-shell structure, which comprises the following steps:
   1) preparation of $Fe_3O_4$ nanoparticles:
      add ferrous sulfate heptahydrate and anhydrous sodium acetate to ethylene glycol according to the mole ratio of ferrous sulfate heptahydrate:anhydrous sodium acetate=1:5 to 8 to obtain an ethylene glycol solution, stir until the ethylene glycol solution is transparent and transfer the ethylene glycol solution to a high pressure reaction vessel and the ethylene glycol solution is sealed in the high pressure reaction vessel for 5 to 8 hours at 150 to 200 DEG C., after centrifugation, washing and drying of the ethylene glycol solution, obtain the $Fe_3O_4$ nanoparticles;
   2) preparation of $Fe_3O_4$@$mSiO_2$ nanoparticles:
      add the $Fe_3O_4$ nanoparticles obtained in step 1) to a mixture of ethanol and water, and disperse ultrasonically, add hexadecyltrimethylammonium bromide and tetraethoxysilane in accordance with the $Fe_3O_4$ nanoparticles:cetyltrimethylammonium bromide:tetraethoxysilane=1:3 to 5:2 to 3 to obtain a $Fe_3O_4$@$mSiO_2$ solution and keep at room temperature for 6 to 10 hours, after magnetic separation, washing and drying of the $Fe_3O_4$@$mSiO_2$ solution, obtain the $Fe_3O_4$@$mSiO_2$ nanoparticles;
   3) preparation of $Fe_3O_4$@$mSiO_2$@MANHE (MANHE: Monomer 4,4-Azobis(4-cyanovaleric acid) 4-vinyl pyridine N-hydroxysuccinimide) nanoparticles:
      add the $Fe_3O_4$@$mSiO_2$ nanoparticles obtained in step 2) to N, N-dimethylformamide, disperse by ultrasonic, add γ-aminopropyltriethoxysilane in accordance with the $Fe_3O_4$@$mSiO_2$ nanoparticles:γ-aminopropyltriethoxysilane=50-100 mg:1 mL to obtain an amino-modified $Fe_3O_4$@$mSiO_2$ solution, stir for 24 hours at room temperature, then centrifuge, wash and dry the amino-modified $Fe_3O_4$@$mSiO_2$ solution to obtain amino-modified $Fe_3O_4$@$mSiO_2$ nanoparticles;
      add the amino-modified $Fe_3O_4$@$mSiO_2$ nanoparticles into cyclohexanone and disperse by ultrasonic, add 4,4'-azobis (4-cyanovaleryl chloride) in accordance with the amino-modified $Fe_3O_4$@$mSiO_2$ nanoparticles: 4,4'-azobis (4-cyanovaleryl chloride)=1:20-30 in mass ratio to obtain an ABCPA (4,4-azobis (4-cyanopentanoicchloride)) modified $Fe_3O_4$@$mSiO_2$ solution, stir for 24 hours at room temperature, and centrifuge, wash and dry the ABCPA modified $Fe_3O_4$@$mSiO_2$ solution to obtain ABCPA modified $Fe_3O_4$@$mSiO_2$ nanoparticles;
      add the ABCPA-modified $Fe_3O_4$@$mSiO_2$ nanoparticles to cyclohexanone and disperse by ultrasonic, add N-acryloyloxysuccinimide and 4-vinylpyridine in accordance with the ABCPA modified $Fe_3O_4$@$mSiO_2$ nano-particles:N-acryloyloxysuccinimide=1:20 to 30 in mass ratio and N-acryloyloxysuccinimide:4-vinylpyridine=1 g:10 to 15 mL to obtain a $Fe_3O_4$@$mSiO_2$@MANHE solution, react at 70-80 DEG C. for 0.5-1 hour, and centrifuge, wash and dry the $Fe_3O_4$@$mSiO_2$@MANHE solution to obtain the $Fe_3O_4$@$mSiO_2$@MANHE nano-particles;
   4) preparation of *Bacillus subtilis*@$Fe_3O_4$@$mSiO_2$@ MANHE composite:
      add *Bacillus subtilis* to a PBS solution and disperse evenly, add the $Fe_3O_4$@$mSiO_2$@MANHE nano-particles obtained in step 3) in accordance with the wet weight of *Bacillus subtilis*:$Fe_3O_4$@$mSiO_2$@MANHE nano-particles=50-100:1 in mass ratio to obtain a *Bacillus subtilis*@$Fe_3O$ $mSiO_2$@ MANHE solution, and place on a constant temperature shaker at 30° C./120 rpm for 24 hours, magnetic centrifuge, wash and dry the *Bacillus subtilis*@$Fe_3O_4$@$mSiO_2$@ MANHE solution to obtain the *Bacillus subtilis* biological composite material loaded with $Fe_3O_4$ magnetic nanoparticles with core-shell structure.

2. The preparation method according to claim 1, wherein the molar ratio between the ferrous sulfate heptahydrate and anhydrous sodium acetate described in step 1) is 1:7.

3. The preparation method according to claim 1, wherein the volume ratio of ethanol to water in the mixture of ethanol and water in step 2) is 4:1; the $Fe_3O_4$ nanoparticles, cetyltrimethylammonium bromide, tetraethoxysilane described in the step 2) is 1:3:2.3.

4. The preparation method according to claim 1, wherein
   the ratio between the $Fe_3O_4$@$mSiO_2$ nanoparticles and the γ-aminopropyltriethoxysilane described in the step 3) is 200 mg:3 mL;
   the mass ratio of the amino-modified $Fe_3O_4$@$mSiO_2$ nanoparticles to 4,4'-azobis (4-cyanovaleryl chloride) in step 3) is 1:20;
   the weight ratio between the ABCPA-modified $Fe_3O_4$@$mSiO_2$ nanoparticles and the N-acryloyloxysuccinimide described in step 3) is 1:20;
   the ratio between N-acryloyloxysuccinimide and 4-vinylpyridine in step 3) is 1 g:10 mL.

5. The preparation method of claim 1, wherein the inert gas in step 3) is selected from any of nitrogen, helium, and argon.

6. The preparation method according to claim 5, wherein the inert gas in step 3) is nitrogen.

7. The preparation method according to claim 1, wherein the mass ratio between the wet weight of *Bacillus subtilis* described in step 4) and the $Fe_3O_4$@$mSiO_2$@MANHE nanoparticles is 100:1.

8. The preparation method according to claim 1, wherein in step 4), the pH of said PBS solution is 7.

9. A *Bacillus subtilis* biological composite material loaded with a $Fe_3O_4$ magnetic nanoparticle having a core-shell structure prepared by the preparation method according to claim 1.

10. A method of treating waste water containing hexavalent chromium comprising applying the *Bacillus subtilis* biological composite material loaded with a $Fe_3O_4$ magnetic nanoparticle having a core-shell structure of claim 9 to the waste water.

* * * * *